United States Patent [19]

Vainberg et al.

[11] Patent Number: 5,068,409
[45] Date of Patent: Nov. 26, 1991

[54] BIS(4-HALO-PHTHALIC ACID) QUARTER SALT, PROCESS FOR THEIR PREPARATION AND THEIR USE

[75] Inventors: Olga Vainberg; Leonard M. Shorr, both of Haifa, Israel

[73] Assignee: Bromine Compounds Ltd., Beer Sheva, Israel

[21] Appl. No.: 579,360

[22] Filed: Sep. 7, 1990

[30] Foreign Application Priority Data

Sep. 8, 1989 [IL]  Israel ........................................ 91563

[51] Int. Cl.[5] ...................... C07C 63/20; C07C 51/41; C07C 51/487
[52] U.S. Cl. ..................................... 562/480; 560/83; 562/485
[58] Field of Search ................... 562/480, 485; 560/83

[56] References Cited

FOREIGN PATENT DOCUMENTS 725605 9/1942 Fed. Rep. of Germany .
798442 7/1958 United Kingdom .

*Primary Examiner*—Jose G. Dees
*Assistant Examiner*—Vera C. Clarke
*Attorney, Agent, or Firm*—Michael N. Meller

[57] ABSTRACT

The bis(4-halo-phthalic acid) quarter salt of formula

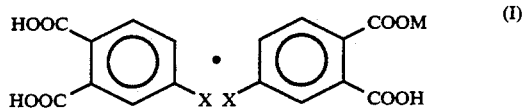

(I)

wherein M is an alkali metal or ammonium, and X is a halogen atom is descibed. Further described is a process for its preparation and a method of purifying 4-halo-phthalic acid containing impurities, which comprises preparing therefrom a compound of formula I, separating the compound of formula I which precipitates from the mother liquor, washing it and recovering the 4-halo-phthalic acid.

8 Claims, 3 Drawing Sheets

BIS(4-HALO-PHTHALIC ACID) QUARTER SALT, PROCESS FOR THEIR PREPARATION AND THEIR USE

FIELD OF THE INVENTION

The present invention relates to a novel bis(4-halo-phthalic acid) quarter salt, to a process for its preparation, and to its use for preparing 4-halo-phthalic acid. The invention is further concerned with a method of purifying 4-halo-phthalic acid solutions containing impurities.

BACKGROUND OF THE INVENTION

Phthalic anhydride (as well as phthalic acid, from which the anhydride is easily prepared) derivatives bearing a reactive group in the 4-position are useful intermediates for the production of high-performance polyimides, which are used in many applications, such as composites, foams, molded articles and microelectronic coatings. These polymers are very useful because of their excellent UV resistance, thermaloxidative stability, chemical resistance and flame retardancy. Polyetherimides have been prepared by nitro-displacement of nitrophthalic anhydride [D. M. White et al., J. Pol. Science 19, 1635 (1981)] as well as by chlorine or fluorine displacement of the corresponding halogenated phthalic derivatives [H. M. Relles, Contemp. Top. Polym. Sci. 5, 261 (1984)]. The 4-halo-derivatives also find use in the manufacture of 4,4'-oxydiphthalic anhydride and of 4,4'-biphenyltetracarboxylic dianhydride, which are combined with diamines to produce heat-resistant polyimide plastics. U.S. Pat. No. 4,697,023 discloses the use of the bromo-derivative, along with chloro- and flouoro- derivatives for the production of oxy-diphthalic anhydrides.

A severe problem, to which the art has so far been unable to provide a solution, is that in the manufacture of 4-substituted phthalic acids and anhydrides the 3-isomers and several disubstituted derivatives are usually produced as undesired by-products. Furthermore, often unreacted phthalic anhydride or acid remains in the final product. This problem exists in all known preparation processes. For instance, the preparation of 4-bromophthalic acid (which will be hereinafter called 4-BrPA, for the sake of brevity) or the anhydride, which are particularly useful intermediates, can be prepared in a number of ways. For example, phthalic acid has been reacted with potassium bromate, to provide a yield of 50% [JACS 46,2169,1981] or with a mixture of an alkali metal bromide and an oxidizing agent such as hypochlorite or hypobromite, or phthalic acid (hereinafter PA) has been brominated in 60% oleum. Metal salts of PA have been brominated in water directly with bromine [U.S. Pat. No. 2,394,268] or in a non-protonic polar solvent, as in Japanese Patent No. 79-29348. In these processes, the product is contaminated to varying degrees with the 3-BrPA isomer, and with di- and higher brominated impurities, depending on the brominating system and conditions employed. In an alternative process [see, e.g., CA 90: 38640e, 1979], brominated xylenes may be oxidized, but 4-bromoxylene is usually contaminated with other mono-brominated xylenes, as well as with higher brominated materials.

Removing the contaminants obtained in the processes of the art is very difficult because of the great similarity of the physical properties of the impurities with those of the desired product, viz., the mono-substituted 4-derivative. For this reason, separating the contaminants from the final product has been industrially impractical. As a result of this fact, substituted PAs normally used are not highly pure, the contents and types of contaminants vary from one batch of material to another, which lead to erratic results and performances of the plastics into which they are incorporated.

It is therefore clear that it would be highly desirable to be able to prepare 4-halo-phthalic acids which are highly pure, by an industrially applicable process. It has now surprisingly been found that it is possible selectively to precipitate 4-mono-halogenated phthalic acids from aqueous solutions containing contaminants, and to prepare highly pure final products, with purities of 99% or higher.

It has further been most surprisingly found that when 4-halo-phthalic acid is precipitated from the aqueous solution, under conditions which will be detailed hereinafter, a novel material is formed, which was so far unknown in the art, which is a bis(4-halo-phthalic acid) quarter salt, viz., a material which is obtained by the formation of a complex of the 4-halophthalic acid with a mono- salt of the diacid with an alkali metal or with ammonium.

It is therefore an object of the present invention to provide novel compounds, which can be termed "quarter salts". It is another object of the present invention to provide a process for preparing such quarter salts.

It is a further object of the invention to provide a process for preparing 4-halo-phthalic acids in very high purity, which is simple, inexpensive and industrially applicable.

It is still another object of the invention to provide a method for purifying 4-halo-phthalic acids which contain impurities, particularly impurities which are not simply separated from the desired halo-substituted phthalic acid.

SUMMARY OF THE INVENTION

The bis(4-halo-phthalic acid) quarter salts of the invention have the formula:

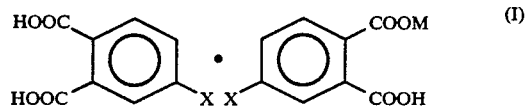

wherein M is an alkali metal or ammonium, and X is a halogen atom. Preferred alkali metals comprise Na, K and Li. Preferred halogens are bromine and chlorine.

The process for preparing a compound of formula I comprises the steps of:

a) providing an aqueous solution containing a 4-halo-phthalic acid and an ion of an alkali metal or an ammonium ion;

b) adjusting the pH of the solution between about 2 and about 3, preferably between 2.1 and 2.8; and c) recovering the compound of formula I which precipitates.

As will be apparent to a skilled chemist, it is preferable that at least 0.25 mole of the alkali metal or ammonium ion be present in solution for each mole of the substituted phthalic acid, for amounts less than this will lead to less than maximum precipitation of the quarter salt.

The 4-halogenated phthalic acid can easily be recovered from the quarter salts of formula I, by reacting it with a water soluble acid which is stronger than phthalic acid. Thus, a method of purifying 4-halo-phthalic acids which contain impurities comprises preparing from the solution containing the 4-halo-phthalic acid a compound of formula I, separating the compound of formula I which precipitates from the mother liquor, washing the same, if necessary, to remove remaining water soluble impurities, and recovering the 4-halo-phthalic acid therefrom, by reacting it with a water-soluble acid which is stronger than phthalic acid.

In the processes detailed above, the concentration of the various organic compounds will normally be in the range of 5–50%, but it is preferable to treat solutions in which these compounds are in a range of 5–30%. The temperatures useful for carrying out the process and method of the invention will be recognized by a person skilled in the art. These temperatures, as will be understood by a skilled chemist, depend on the concentration of the ingredients, and may range, e.g., from ambient temperature or below, to 60° C. or higher.

As will be appreciated by a skilled chemist, it is very surprising that in the pH range of the invention, the 4-halo PAs precipitate as 1:1 complexes of their mono-salts and the free diacid (which, for the sake of brevity, will be referred to hereinafter as the Quarter Salts, or QSs. The inventors have found that neither the 4-nitro-PA, PA itself or the 3-halo-PAs form similar QSs. Because of the low solubility of the QS, which is much lower in water than that of the contaminants, formation of the QS is an easy and convenient means of selectively precipitating the pure 4-halo-PA, while leaving the contaminants in solution.

As will be apparent to a skilled chemist, this purification process, the formation of the compound of formula I, and all the steps detailed herein can be effected either as a further step in the preparation of the 4-halo-PAs, after halogenation has been completed, or as a purification step of an already-formed product, which has been recovered from a halogenation process elsewhere. Thus, for example, when the metal salts of PA are brominated in water directly with bromine, as taught in U.S. Pat. No. 2,394,268, at the termination of the bromination reaction the corresponding QS can be selectively precipitated by adjusting the pH of the mixture, as hereinbefore detailed. In this way, pure 4-BrPA is produced directly.

In the following examples, given for the purpose of illustration, and without the intention of limiting the invention in any way, the product has been analyzed also to show that it does not consist of a 1:1 mixture of the 4-halo-PA with its mono-salt, but rather that the QS is a novel and unique compound. This can be appreciated by inspection of the figures appended hereto, which are briefly detailed hereinafter:

The spectra were obtained using the following instruments: XRD—a Rigaku D-Max-IIIC wide angle diffractometer using $CuK_\alpha, \lambda = 1.5406$ Å, 45 KV, 30 mA, scan speed 2 degrees/min IR—Nicolet Model 5MX

EXAMPLES 1-12

Solutions of phthalic anhydride in aqueous NaOH were brominated essentially as described in U.S. Pat. No. 2,394,268, to produce the mixed products shown in Table I. A typical reaction is described below.

326 Parts of phthalic anhydride were added to 665 parts of water, and the temperature raised to 50° C. Caustic soda (176 parts, as a 50% aqueous solution) was then added until all the phthalic acid dissolved. The solution was then cooled to 30° C. and bromination was effected in 3 steps. In the first step, 176 parts of bromine were added over a 1 hour period, maintaining the temperature at 30° C. The temperature was then gradually raised to 95° C. and maintained at that level for approximately one hour more. The mixture was then cooled to 80° C. and a second portion of 45–50 parts of caustic soda (as a 50% aqueous solution) were added. The charge was again cooled to 30° C. and bromination continued with 117 parts of bromine, followed by the addition of 25–30 parts of caustic soda. In the final step, 88 parts of bromine were added over a 30 minute period, at 30° C., the temperature was raised to 95° C. within one hour, and held at that temperature for 30 minutes.

Following the bromination reaction, nitrogen was bubbled through the hot reaction mixture to remove most of the excess bromine, and then sodium bisulfite was added to neutralize the residual unreacted bromine.

Figure 1:
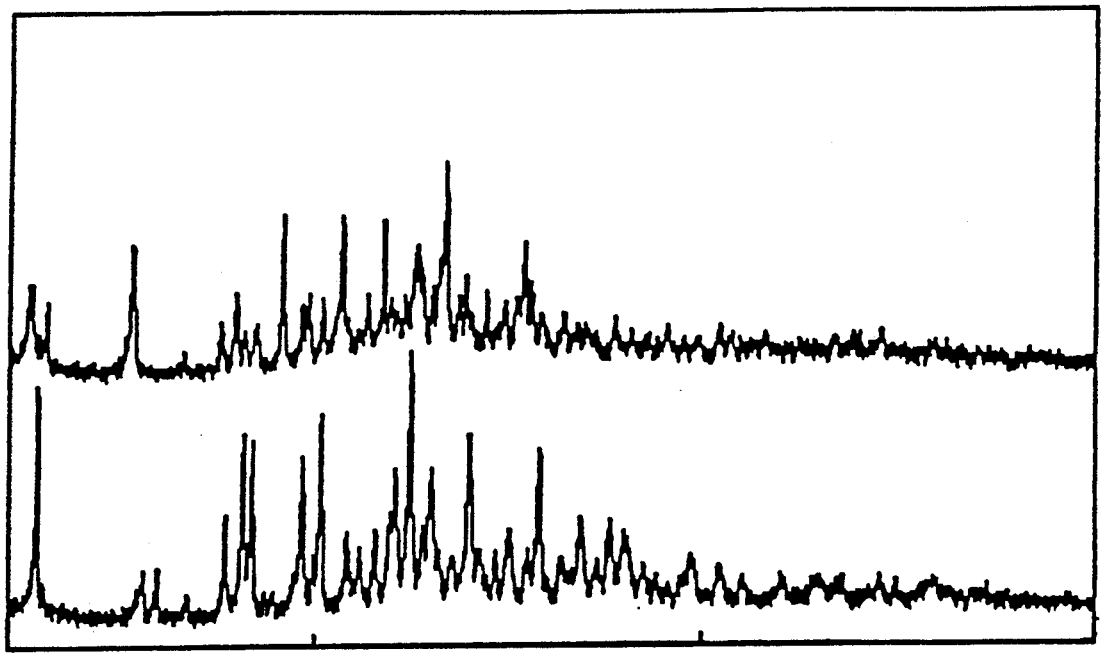
FIG. 1 is the X-ray powder diffraction pattern (XRD) of a mixture of 4-BrPA and its mono-Na salt, indicated by 2, compared with that of the sodium Quarter Salt (Na QS), indicated by 1. It is easily seen that the XRDs belong to different materials.
Figure 5:
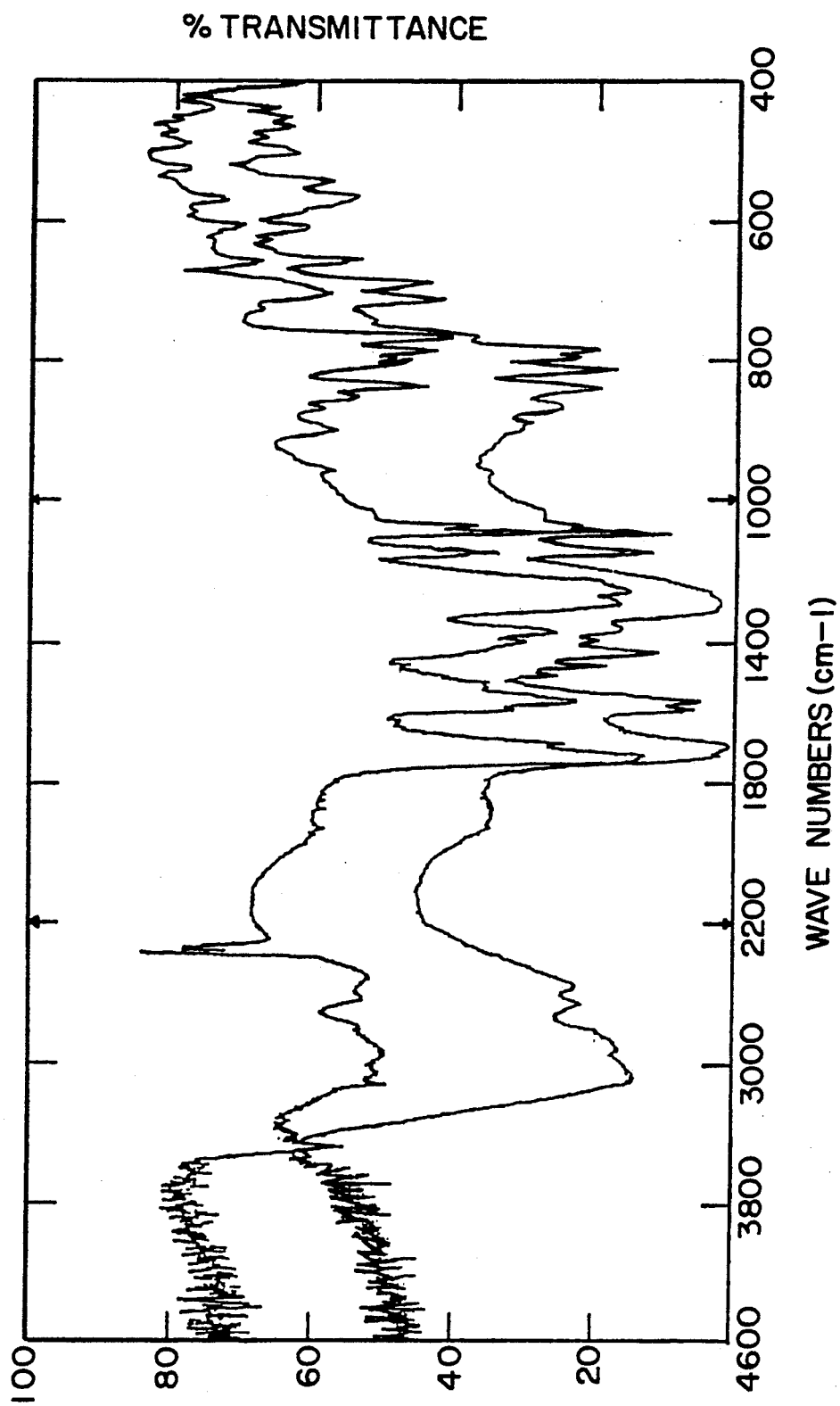
FIG. 5 is the IR spectrum of a mixture of 4-BrPA with its mono-Na salt, compared with that of the Na QS (lines 2 and 1 respectively). Here again, the difference between the two examined materials is clear.

Crystallization was effected under various conditions of concentration, pH and temperature, as shown in Table I. It can be seen that when operating according to the invention, pure 4-BrPA precipitates as its Na QS. One of these crystalline precipitates typically served to obtain the X-Ray Diffraction pattern and IR spectra shown in FIGS. 1 and 5.

As can be seen from the comparison Example 1 in Table I, precipitation above pH 3.0, i.e., at pH 3.8, yields a contaminated precipitate. If, on the other hand, the solution is acidified to pH values below 2, essentially all of the (mixed) free acids precipitate.

Example 12 of Table I demonstrates the conversion of the free acid to the Na QS, and is given for comparison.

EXAMPLE 13

Purification of Contaminated 4-BrPA

An impure 4-BrPA of the following composition was submitted to purification:

| | |
|---|---|
| 4-BrPA | 91.5% |
| 3-BrPA | 2.9 |
| PA | 5.0 |

| -continued | |
|---|---|
| Di BrPA | 0.7 |

A slightly basic 23.5% solution of this mixture in water (pH 9.0) was prepared at a temperature sufficiently high to effect dissolution. The mixture was cooled to ambient temperature and the pH was adjusted to 2.35. The 4-BrPA precipitated in an 82% yield as the Na QS, as shown by its Na content of 4.8% (calcd. 4.5%) and the ratio of primary to secondary H ions of 0.193:0.575 (calcd. 1:3). The acid was liberated from the salt by acidification to pH 1, extracted by ethyl acetate and analyzed by GC. It was found to contain 99.5% 4-BrPA.

EXAMPLE 14

Precipitation of the 4-BrPA Potassium QS

Figure 2:
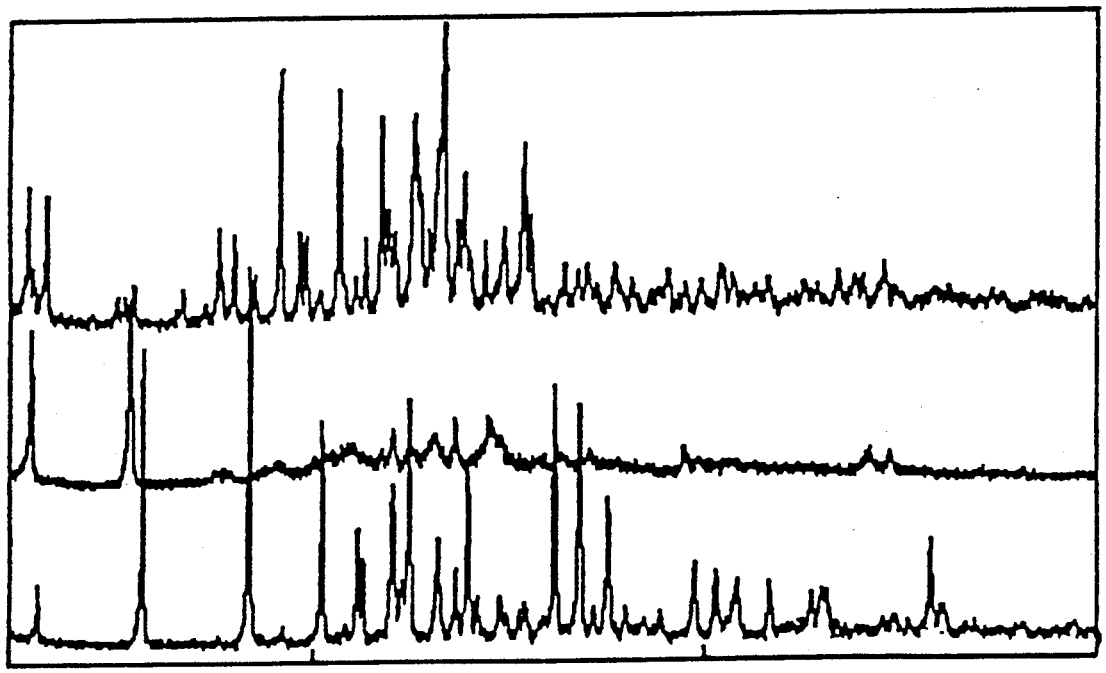
FIG. 2 shows the XRD patterns for the mono-K salt, indicated by 2, the free acid, indicated by 3, and the potassium Quarter Salt (K QS), indicated by 1. Here again, the XRD is different in each case.

An impure mixture of 4-BrPA (89.5%), 3-BrPA (2.8%) and PA (7.5%) was dissolved in an equimolar KOH solution in hot water (22.3% total solids concentration). The pH was adjusted to 2.4 with concentrated HCl, and cooled to ambient temperature. The crystals which precipitated contained 99.6% 4-BrPA (determined by GC) as the potassium QS, recovered in an 80% yield. It contained 7.1% K (calcd. 7.4%). The ratio of its primary to secondary H ions was 0.194:0.569 (calcd. 1:3). Its XRD spectrum is seen to be different from that of an equimolar mixture of the mono-K salt and the free dibasic acid as shown in FIG. 2.

EXAMPLE 15

Precipitation of the 4-BrPA Lithium QS

Figure 3:
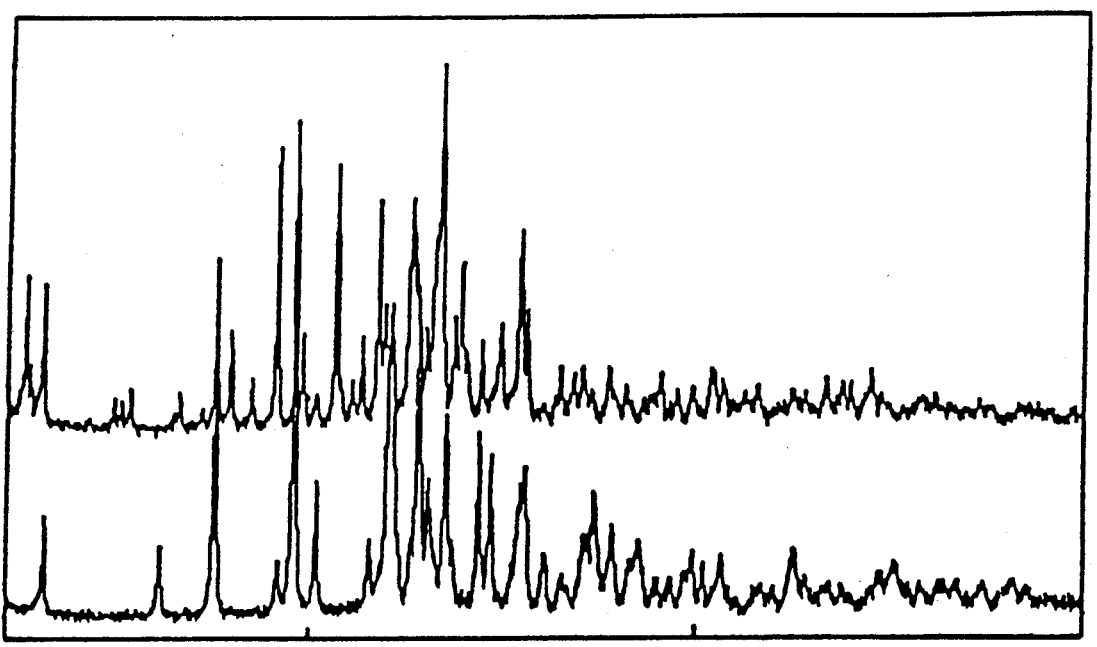
FIG. 3 shows the XRD patterns for the lithium Quarter Salt (Li QS), indicated by 1, and of the free acid, indicated by 2. This figure, as the others, clearly shows the difference between the materials.

The same mixture of 4-BrPA as used in Example 12 (39.2 g. 0.16 mole) was dissolved in hot water (203 ml) containing 3.4 g (0.08 mole) of LiOH. The pH was adjusted to 2.55 with concentrated HCl, and the mixture was allowed to cool to room temperature. The crystals which precipitated contained 99% pure 4-BrPA as its Li QS (1.4% Li, calcd. 1.4%). The ratio of its primary to secondary H ions was 0.206:0.603 (calcd. 1:3). These crystals are clearly neither the mono-lithium salt, which does not precipitate from solutions of the concentration used, nor the free dibasic acid as seen by the comparison of its XRD spectrum with that of the precipitate formed at pH 2.55 (FIG. 3).

EXAMPLE 16

Precipitation of the 4-ClPA Na QS

A commercial sample of 4-ClPA (ex Aldrich) of the following composition

Figure 4:
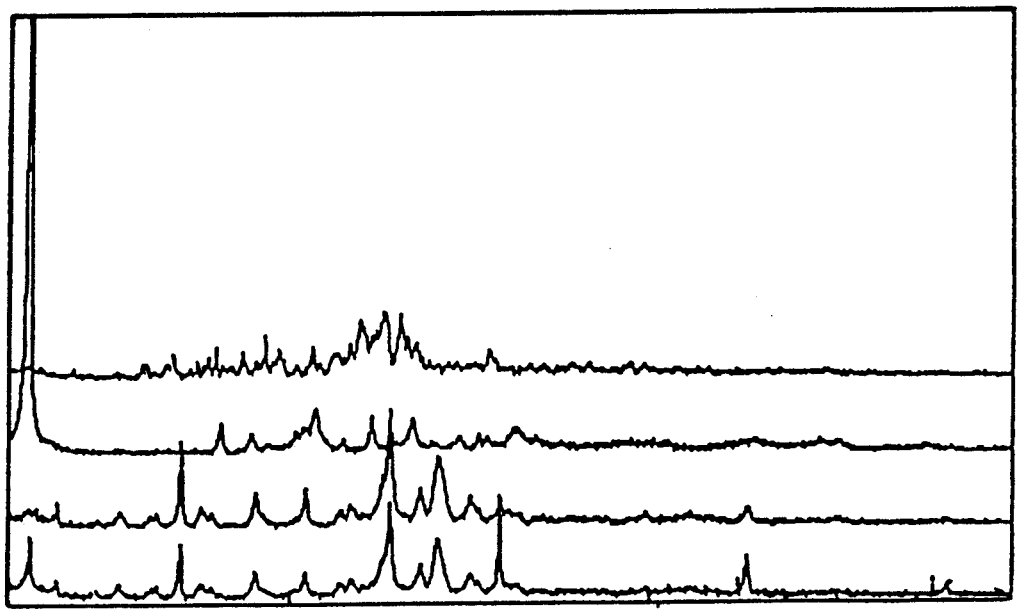
FIG. 4 shows the XRD patterns of the mono-sodium salt, indicated by 3, the Na QS before and after recrystallization from water, indicated by 1 and 2 respectively, and the free acid of 4-chloro-phthalic acid, indicated by 4.

| 80.0% | 4-ClPA |
|---|---|
| 3.7 | 3-ClPA |
| 10.7 | PA |
| 5.6 | Di ClPA | was dissolved in an equimolar aqueous solution of NaOH at elevated temperature. The pH was adjusted to 2.3 by the addition of concentrated HCl and then the mixture was cooled to ambient temperature. The crystals which precipitated contained 93.4% of the 4-Cl isomer and 5.3% Na (calcd. for the QS, 5.4%). Its XRD spectrum is compared with those of the monosodium salt and the free dibasic acid in FIG. 4 and shown to be different from both.

EXAMPLE 17

Precipitation of the 4-BrPA Ammonium QS

Example 15 was repeated, but using ammonium hydroxide instead of LiOH. Precipitation was done at pH 3.08. The 4-BrPA ammonium QS which precipitated contained 3.56, 3.54% NH4+ (based on the amount of NH3 liberated upon treatment with strong base); calc'd. 3.55%. H(1): Htot was 0.197:0.576.

While the above examples have been provided to show the use of different cations, it is clear that mixtures of different hydroxides can be used, to obtain mixed QS salts, although the use of mixtures, rather than substantially pure hydroxides, does not present any particular process advantage.

TABLE I

The recovery of 4-BrPA from PA Bromination Products

| Ex. No. | Initial Composition (Wt. %) | | | | Crystallization Conditions | | | Product Composition* | | |
|---|---|---|---|---|---|---|---|---|---|---|
| | 4-BrPA | 3-BrPA | PA | Di BrPA | wt % Concn.*** | pH | °C. | % Na | H (1):Htot | % 4BrPA |
| 1 | 84.6 | 8.1 | 7.1 | nd | 12 | 3.8 | RT | | | 80.2 |
| 2 | 75.3 | 14.8 | 8.7 | 1.0 | 16 | 2.3 | RT | 4.7 | | 99.5 |
| 3 | 83.4 | 7.9 | 5.7 | nd | 14 | 2.3 | RT | 4.9 | | 99.9 |
| 4 | 88.8 | 3.9 | 4.9 | nd | 14 | 2.3 | RT | 4.7 | .198:.574 | 99.9 |
| 5 | 80.0 | 12.4 | 7.4 | <1 | 15 | 2.3 | RT | 4.7 | | 99.0 |
| 6 | 82.5 | 12.1 | 5.4 | nd | 16 | 2.4 | 55 | | .185:.561 | 99.5 |
| 7 | 83.0 | 8.5 | 8.2 | 0.3 | 18 | 2.5 | 50 | | | 99.8 |
| 8 | 83.0 | 8.5 | 8.2 | 0.3 | 18 | 2.5 | 10 | | .195:.575 | 99.4 |
| 9 | 75.0 | 14.8 | 8.7 | 1.0 | 16 | 2.3 | RT | 4.6 | | 99.5 |
| 10 | 63.1 | 13.0 | 16.7 | 7.2 | 15 | 2.1 | 55 | | | 97 |
| 11 | 91.5 | 2.8 | 4.9 | 0.8 | 22 | 2.3 | RT | 4.4 | .193:.575 | 99.5 |
| 12** | 99.2 | 0.2 | 0.4 | 0.2 | 18 | 2.6 | RT | 4.5 | .195:.576 | 99.9 |

*Recoveries ranged from 73-82%
**Conversion of the free diacid to the Na QS
***Concentration of organic components in the solution before crystallization
nd = not detected
RT = Ambient Temperature

We claim:
1. The bis(4-halo-phthalic acid) quarter salt of the formula

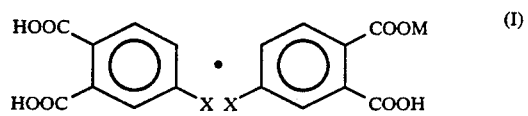

wherein M is an alkali metal or ammonium ion, and X is a halogen atom.

2. A process for preparing a compound of Formula I

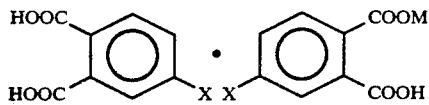

wherein M is an alkali metal or ammonium ion, and X is a halogen atom, comprising the steps of:

a) providing an aqueous solution containing a 4-halo-phthalic acid and an ion of an alkali metal or an ammonium ion;

b) adjusting the pH of the solution between about 2 and about 3; and c) recovering the compound of formula I which precipitates.

3. A process according to claim 2, wherein the halogen is selected from the group consisting of Br and Cl.

4. A process according to claim 2, wherein the pH is adjusted to between 2.1 and 2.8.

5. A process for preparing 4-halo-phthalic acid, comprising reacting a compound of Formula I

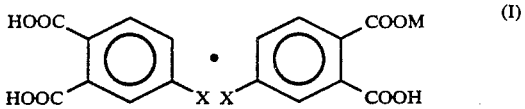

wherein M is an alkali metal or ammonium ion, and X is a halogen atom, with a water soluble acid which is stronger than phthalic acid.

6. A process according to claim 5, wherein the halogen is selected from the group consisting of Br and Cl.

7. A method of purifying 4-halo-phthalic acid containing impurities, comprising preparing therefrom a compound of Formula I,

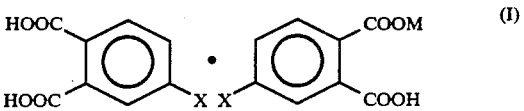

wherein M is an alkali metal or ammonium ion, and X is a halogen atom;

a) providing an aqueous solution containing a 4-halo-phthalic acid and an ion of an alkali metal or an ammonium ion;

b) adjusting the pH of the solution between about 2 and about 3, and separating the compound of formula I which precipitates from the mother liquor, washing the same to remove any remaining water-soluble impurities and recovering the 4-halo-phthalic acid therefrom.

8. A method according to claim 7, wherein the halogen is Br or Cl.

* * * * *